United States Patent
Park et al.

(10) Patent No.: US 7,378,267 B1
(45) Date of Patent: May 27, 2008

(54) METHOD FOR L-THREONINE PRODUCTION

(75) Inventors: Jae Yong Park, Seoul (KR); Byoung Choon Lee, Seoul (KR); Dae Cheol Kim, Yicheon (KR); Jin Ho Lee, Yicheon (KR); Jae Yong Cho, Yongin (KR); Young Hoon Park, Seongnam (KR)

(73) Assignee: Cheil Jedang Corporation, Seoul (KR)

( * ) Notice: Subject to any disclaimer, the term of this patent is extended or adjusted under 35 U.S.C. 154(b) by 282 days.

(21) Appl. No.: 10/508,728

(22) PCT Filed: May 16, 2002

(86) PCT No.: PCT/KR02/00920

§ 371 (c)(1),
(2), (4) Date: Sep. 21, 2004

(87) PCT Pub. No.: WO03/080843

PCT Pub. Date: Oct. 2, 2003

(51) Int. Cl.
*C12N 1/12* (2006.01)
*C12P 13/04* (2006.01)

(52) U.S. Cl. .................. 435/252.1; 435/106

(58) Field of Classification Search .......... None
See application file for complete search history.

(56) References Cited

U.S. PATENT DOCUMENTS

| | | | |
|---|---|---|---|
| 5,149,784 A | 9/1992 | Chu | |
| 5,258,495 A | 11/1993 | Chu | |
| 5,538,873 A | 7/1996 | Debabov et al. | |
| 5,574,135 A | 11/1996 | Chu | |
| 5,939,307 A | 8/1999 | Wang et al. | |

FOREIGN PATENT DOCUMENTS

| | | |
|---|---|---|
| JP | 02-219582 | 9/1990 |
| KR | 10-1992-0008365 B1 | 9/1992 |
| KR | 10-2002-0066662 A | 8/2002 |
| WO | WO 93/21207 A1 | 10/1993 |

OTHER PUBLICATIONS

Hashiguchi et al., Biosci. Biotech. Biochem., 1997, 61(1): 105-108.*

Merkel, A. et al., *Purification, crystallization and preliminary structural studies of dTDP-4-keto-6-deoxy-glucose-5-epimerase (EvaD) from Amycolatopsis orientalis, the fourth enzyme in the dTDP-L-epivancosamine biosynthetic pathway*, Acta Crystallographica Section D Biological Crystallography, vol. 58, No. 7, pp. 1226-1228 (2002).

Chinchilla, D. et al., *Amino Acid Substitutions in the C-terminal Regulatory Domain Disrupt Allosteric Effector Binding to Biosynthetic Threonine Deaminase from Escherichia coli*, The Journal of Biological Chemistry, Sep. 1998, pp. 23219-23224, vol. 273(36).

Crout, D., et al., *Stereochemistry of the Conversions of L-Threonine and D-Threonine into 2-Oxobutanoate by the L-Threonine and D-Threonine Dehydratases of Serratia marcescens*, Eur. J. Biochem., 1980, pp. 97-105. vol. 106.

Datta, P., et al., *Covalent Structure of Biodegradative Threonine Dehydratase of Escherichia coli: Homology with Other Dehydratases*, Proc. Natl. Acad. Sci. USA, Jan. 1987, pp. 393-397, vol. 84.

Hofmeister, A., et al., *L-Serine and L-Threonine Dehydratase from Clostridium propionicum: Two Enzymes with Different Prosthetic Groups*; Eur. J. Biochem., 1993, pp. 341-349, vol. 215.

Pagani, R., et al., *The Inhibition of Rat Liver Threonine Dehydratase by Carbamoyl-phosphate: The Formation of Carbamoylpyrdoxal 5'-phosphate*, Biochemica et Biophysica Acta., 1991, pp. 233-240, vol. 1077.

Sahm, H. et al., *Contruction of L-Lysine-, L-Threonine-, or L-Isoleucine-Overprodcing Strains of Corynebacterium glutamicum*, Annals New York Academy of Sciences, pp. 25-39.

* cited by examiner

*Primary Examiner*—Richard Hutson
*Assistant Examiner*—Jae Wan Lee
(74) *Attorney, Agent, or Firm*—Rothwell, Figg, Ernst & Manbeck, PC

(57) ABSTRACT

A method for producing L-threonine using a microorganism is provided. In the method, the threonine dehydratase (tdc) gene existing in the genomic DNA of the microorganism is partially deactivated using a recombination technique. For a microorganism strain with enhanced activity of threonine operon-containing enzymes and the phosphoenolpyruvate carboxylase (ppc) gene, the tdc gene engaged in one of the four threonine metabolic pathways is specifically deactivated, thereby markedly increasing the yield of L-threonine.

2 Claims, 3 Drawing Sheets

SEQUENCE LISTING

<160> NUMBER OF SEQ ID NOS: 2

<210> SEQ ID NO 1
<211> LENGTH: 30
<212> TYPE: DNA
<213> ORGANISM: Artificial sequence
<220> FEATURE:
<223> OTHER INFORMATION: oligonucleotide primer with homology to E. coli

<400> SEQUENCE: 1
aggaggggat ccggtatgtc ttctgaggcg                30

-continued

```
<210> SEQ ID NO 2
<211> LENGTH: 29
<212> TYPE: DNA
<213> ORGANISM: Artificial sequence
<220> FEATURE:
<223> OTHER INFORMATION: oligonucleotide primer with homology to E. coli

<400> SEQUENCE: 2
aggagggaat tcatcggcaa caggcacag                                          29
```

METHOD FOR L-THREONINE PRODUCTION

TECHNICAL FIELD

The present invention relates to the production of L-threonine involving microorganisms. More particularly, the present invention relates to a process for producing L-threonine with a high yield using a microorganism, in which the threonine dehydratase (tdc) gene of the genomic DNA of the microorganism is partially deactivated using a recombination technique to thereby markedly increase the yield of L-threonine.

BACKGROUND ART

L-threonine, a kind of essential amino acid, is widely used as an additive to animal feed and food, and as fluids and synthetic materials for medical and pharmaceutical use. L-threonine is produced by fermentation using synthetic mutants derived from wild types of *Escherichia Coli*, *Corynebacterium*, *Serratia*, and *Providencia*. These mutants are known to include amino acid analogs- and pharmaceutical-resistant mutants and synthetic mutants thereof rendered auxotrophic for diaminopimelic acid, methionine, lysine, or isoleucine (Japanese Laid-open Patent Application No. hei 2-219582, *Appl., Microbiolo. Biotechnol.*, 29, 550-553 (1988), and Korean Patent Publication No. 92-8365). Korean Patent Application No. 90-22965 discloses the L-threonine-producing strain TF4076 (KFCC10718) that is auxotrophic for methionine and resistant to threonine analogs (AHV: α-amino-β-hydroxyvaleric acid), lysine analogs (AEC: S-(2-aminoethyl)-L-cysteine), isoleucine analogs (α-aminobutyric acid), and methionine analogs (ethionine).

A common approach to increase the level of expression of a particular gene uses a plasmid that gives a greater copy number to a microorganism in order to increase the number of genes in the microorganism (Sambrook et al., *Molecular cloning, Second Edition*, 1989, 1.3-1.5). A target gene is integrated into a plasmid, and the host microorganism is transformed with the recombinant plasmid to cause an increase in the number of genes in the host microorganism according to the copy number of the plasmid. A partial success in this type of approach to improve threonine productivity is reported in U.S. Pat. No. 5,538,873. However, most technologies using such recombinant plasmids overexpress a particular gene, which is undesirable for the host microorganism, and causes a problem of plasmid instability so that the plasmid may be lost during cultivation of the recombinant strain.

To address this problem, approaches to add antibiotics to culture media or to use an expression regulatory plasmid were suggested (Sambrook et al. *Molecular cloning, Second Edition*, 1989, 1.5-1.6 & 1.9-1.11). In the approach of using the expression regulatory plasmid to yield a particular product, cell cultivation is performed under non-expression conditions in the growth stage to reduce disadvantages to the host microorganism and transient expression is induced after full growth of the microorganism. However, most of these expression regulatory plasmids may be used only in the case that the final product is protein.

Producing primary metabolites is closely associated with the growth of microorganisms, so it is difficult to increase the yield of the primary metabolites unless target genes are expressed in the growth stage. The production of threonine, a primary metabolite, is such a case.

As an effort to compensate for this drawback, a particular threonine biosynthetic gene was incorporated into a chromosomal DNA to produce threonine (U.S. Pat. No. 5,939,307). However, this approach replaces a chromosomal gene by an inducible promoter-substituted gene, which is hardly expected to markedly increase the expression of the threonine operon gene.

Therefore, the present inventors completed the present invention by inactivating threonine dehydratase (tdc) gene in the chromosome, which involves in one of the threonine degradation pathways, to inhibit the degradation of threonine while the other inherent generic function of the host microorganism remains and thus increase the yield of threonine.

Most current genetic engineering techniques applied to increase the yield of threonine are focused on the biosynthetic pathway starting with oxaloacetate. However, the present invention involves also the activity of threonine dehydratase (tdc) gene in a threonine degradation pathway to efficiently and markedly increase L-threonine yield.

DISCLOSURE OF THE INVENTION

To solve the above-described problems, it is an object of the present invention to provide a high-yield L-threonine production method which eliminates problems of plasmid instability and microbial growth inhibition arising with recombinant plasmid-bearing strains and markedly increases L-threonine productivity by suppressing the activity of a threonine dehydratase.

To achieve the object of the present invention, there is provided a recombinant plasmid incorporating a deactivated tdc (threonine dehydratase) gene.

In one embodiment of the present invention to achieve the object, the tdc operon of a threonine-producing microorganism may be deactivated by cleaving a site in tdc B and tdc C of the tdc operon and inserting a cassette with an antibiotic marker into the cleavage site. Preferably, the threonine producing microorganism is an *E. coli* strain.

In another embodiment of the present invention, the *E. coli* strain may be resistant to threonine analogs, lysine analogs, isoleucine analogs, and methionine analogs. In still another embodiment of the present invention, additional one or more copies of each of the phosphoenolpyruvate carboxylase (ppc) gene and the threonine operon are integrated into the chromosomal DNA of the *E. coli* strain. Preferably, the *E. coli* has the name pGmTN-PPC12 of Accession No. KCCM-10236.

The present invention also provides an *E. coli* strain transformed with the recombinant plasmid described above. A tdc B and tdc C gene fragment including an antibiotic marker originated from the recombinant plasmid may be inserted into the genome of the *E. coli* strain. Preferably, the tdc B and tdc C gene fragment including the antibiotic marker is Δtdc::loxpKan of FIG. 2. Most preferably, the *E. coli* strain has the name TRN212 of Accession No. KCCM-10353.

The object of the present invention is achieved by a method for producing L-threonine using the *E. coli* strain described above, preferably, having the name TRN212 of Accession No. KCCM-10353.

The present invention will now be described in greater detail.

There are a few known L-threonine metabolic pathways (Neihardt F C et al. (eds) *Escherichia coli* and *Salmonella*: Cellular and Molecular Biology, $2^{nd}$ edn. ASM Press., Washington D.C., pp 369-370), including three major pathways:

a first pathway involving threonine dehydrogenase that catalyzes the decomposition of threonine to α-amino-β-ketobutyrate which is then converted into acetyl-CoA and glycine, or decomposed further to form aminoacetone and converted to pyruvate; a second pathway involving threonine dehydratase which generates α-ketobutyrate to be metabolized to propionyl-CoA and finally to succinyl-CoA, an intermediate of the TCA cycle; and a third pathway involving threonine aldolase.

The present invention is characterized in that the activity of the threonine dehydratase in the L-threonine metabolic pathway is suppressed to cause maximum accumulation of L-threonine.

In the L-threonine production method according to the present invention, pGmTN-PPC12 (KCCM-10236, Korean Patent Application No. 01-6976 filed by the applicant) derived from the *E. coli* TF4076 (KFCC10718, Korean Patent Application No. 90-22965) was used as a L-threonine producing strain. The pGmTN-PPC12 strain (KCCM-10236) is obtained by inserting a phosphoenolpyruvate carboxylase (ppc) gene from the chromosome of the L-threonine producing *E. coli* strain, TF4076 (KFCC 10718), by polymerase chain reaction (PCR) and a threonine operon cloned from the same chromosome into the chromosome of the host *E. coli* strain TF4076, so that there are twice as many ppc gene and threonine operon in the chromosomal DNA as there are in the TF4076 strain. The pGmTN-PPC12 strain can enhance the expression of the ppc gene involved in the conversion of phosphoenolpyruvate (PEP) to a threonine biosynthesis precursor, oxaloacetete, and the genes encoding enzymes involved in the synthetic pathway of threonine from oxaloacetate, including thrA (aspartokinase I-homoserine dehydrogenase), thrB (homoserine kinase), and thrC (threonine synthase), and thus can improve L-threonine productivity. The pGmTN-PPC12 strain was deposited Jan. 5, 2001 with the Korean Collection for Type Cultures (KCTC) and was given Accession Number KCCM 10236.

In the present invention, the threonine dehydratase (tdc) gene, which engages in a threonine metabolic pathway of pGmTN-PPC12 (KCCM-10236), is deactivated, to thus increase the yield of L-threonine.

Threonine dehydratase is known to be an operon to express under low-level of oxygen and high-level of threonine concentration conditions. The expression of the tdc operon is also induced at low-glucose content as in the latter half of fermentation. Therefore, it is necessary to deactivate the threonine dehydratase to discover high-throughput threonine producing strains.

BEST MODE FOR CARRYING OUT THE INVENTION

The L-threonine producing method according to the present invention will be described in greater detail.

1. Construction of Recombinant Plasmid

Chromosomal DNA is isolated from a threonine producing strain. By using the chromosomal DNA as a template, recombinant plasmid pT7Blue/tdc including tdc B and tdc C of the tdc operon is obtained. Any cloning vector can be used without limitation, but pT7Blue cloning vector is preferred.

Recombinant plasmid pT7Δtdc::loxpKan containing a defective tdc gene is obtained by integrating a kanamycin-resistant gene fragment including lox p sites into the recombinant plasmid pT7Blue/tdc.

2. Integration of Recombinant Plasmid and Screening

Figure 2:
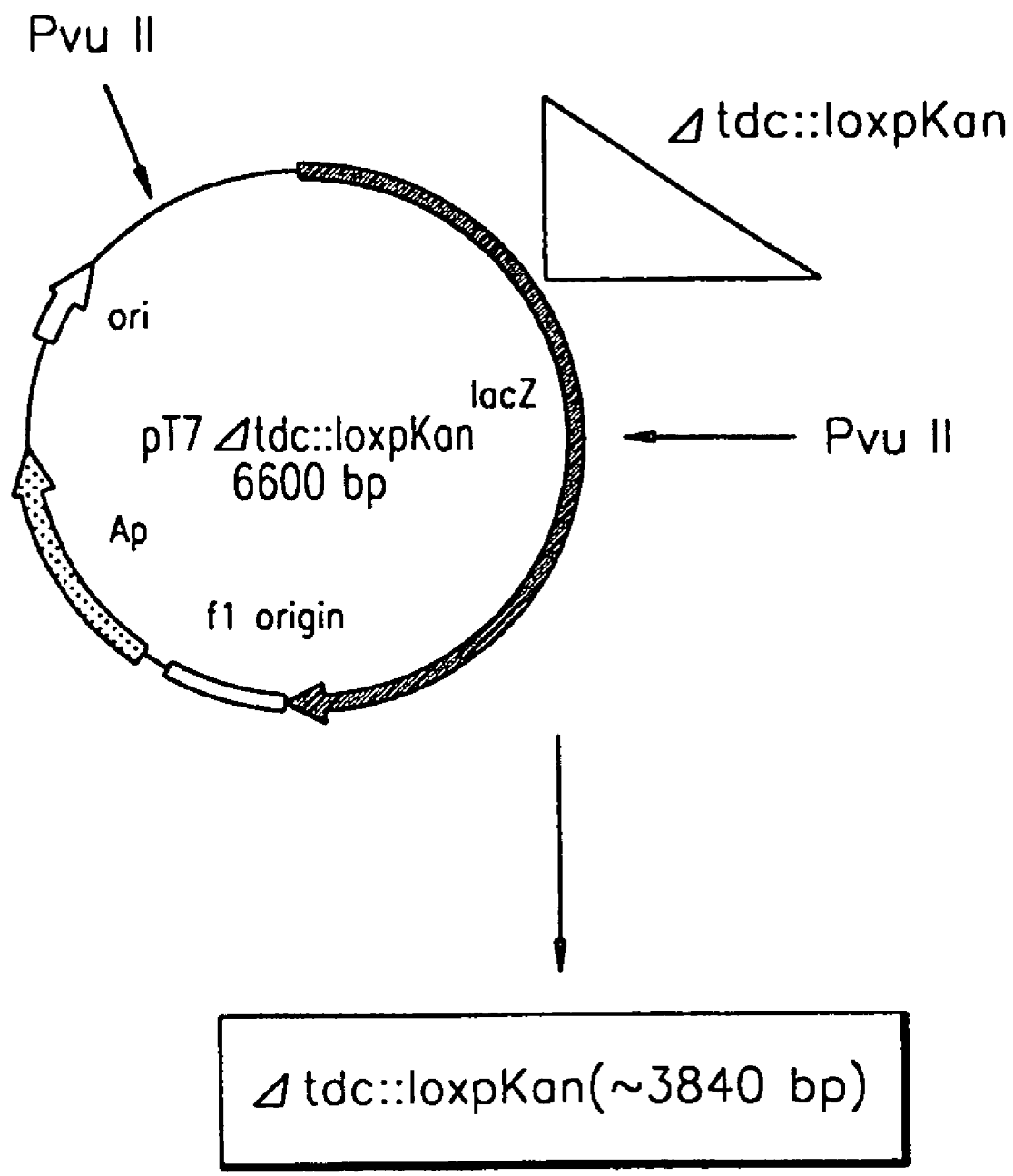
FIG. 2 depicts the process of constructing recombinant plasmid pT7Δtdc::loxpKan and DNA fragment Δtdc::loxp-Kan.

*E. coli* is transformed with the recombinant plasmid pT7Δtdc::loxpKan. Plasmid DNA is isolated and digested with a restriction enzyme, and DNA fragments (Δtdc::loxpKan) are isolated from the digest by electrophoresis. This process is illustrated in FIG. 2.

The threonine producing strain is transformed with the resulting DNA fragment Δtdc::loxpKan. This transformation is performed via homologous recombination which allows the replacement of the inherent tdc gene region of the *E. coli* strain with the recombinant DNA fragment pT7Δtdc::loxpKan.

The resulting transformant is inoculated on a kanamycin-containing solid medium to collect colonies. Finally, a target recombinant strain containing a deactivated tdc gene is obtained.

For the recombinant strain, the tdc gene remains deficient despite the proliferation of the strain, with an excellent L-threonine productivity of 20% higher than the host strain.

The recombinant plasmid can be collected from the transformed strain using known methods, for example, using alkali solution (Sambrook et al., Molecular Cloning, Vol. 1, 1.25-1.28). In particular, Solution 1 (50 mM glucose, 25 mM Tris-HCl, and 10 mM EDTA) is added to weaken the cell membrane of the transformant, and Solution 2 (0.2N NaOH, 1% SDS) is added to destruct the cell membrane and denaturate the cellular constituents of protein and chromosome, and Solution 3 (5M potassium acetate, acetic acid) is added to coagulate the constituents except for the recombinant plasmid. The recombinant plasmid fraction is separated by centrifugation, and only the recombinant plasmid is precipitated with an addition of ethanol and recovered.

The present invention will be described with reference to the following examples. The following examples are for illustrative purposes and are not intended to limit the scope of the invention.

EXAMPLE 1

Construction of Recombinant Plasmid and Knock-out of tdc Gene Using the Recombinant Plasmid The genomic DNA of pGmTN-PPC (KCCM-10236), a threonine producing strain, was isolated using a QIAGEN Genomic-tip system. A gene fragment of 3.1 kb of the tdc operon (5295 bp) that contains the tdc B and tdc C was amplified through polymerase chain reaction (PCR) by using the genomic DNA as a template. The primers used were 5'-agg agg gga tcc ggt atg tct tct gag gcg-3' [SEQ ID NO: 1] and 5'-agg agg gaa ttc atc ggc aac agg cac ag-3' [SEQ ID NO: 2]. The PCR was achieved through 30 cycles of amplification, each cycle including denaturation at 94° C. for 30 seconds, annealing at 56° C. for 30 seconds, and extension at 72° C. for 3 minutes and 30 seconds.

Figure 1:
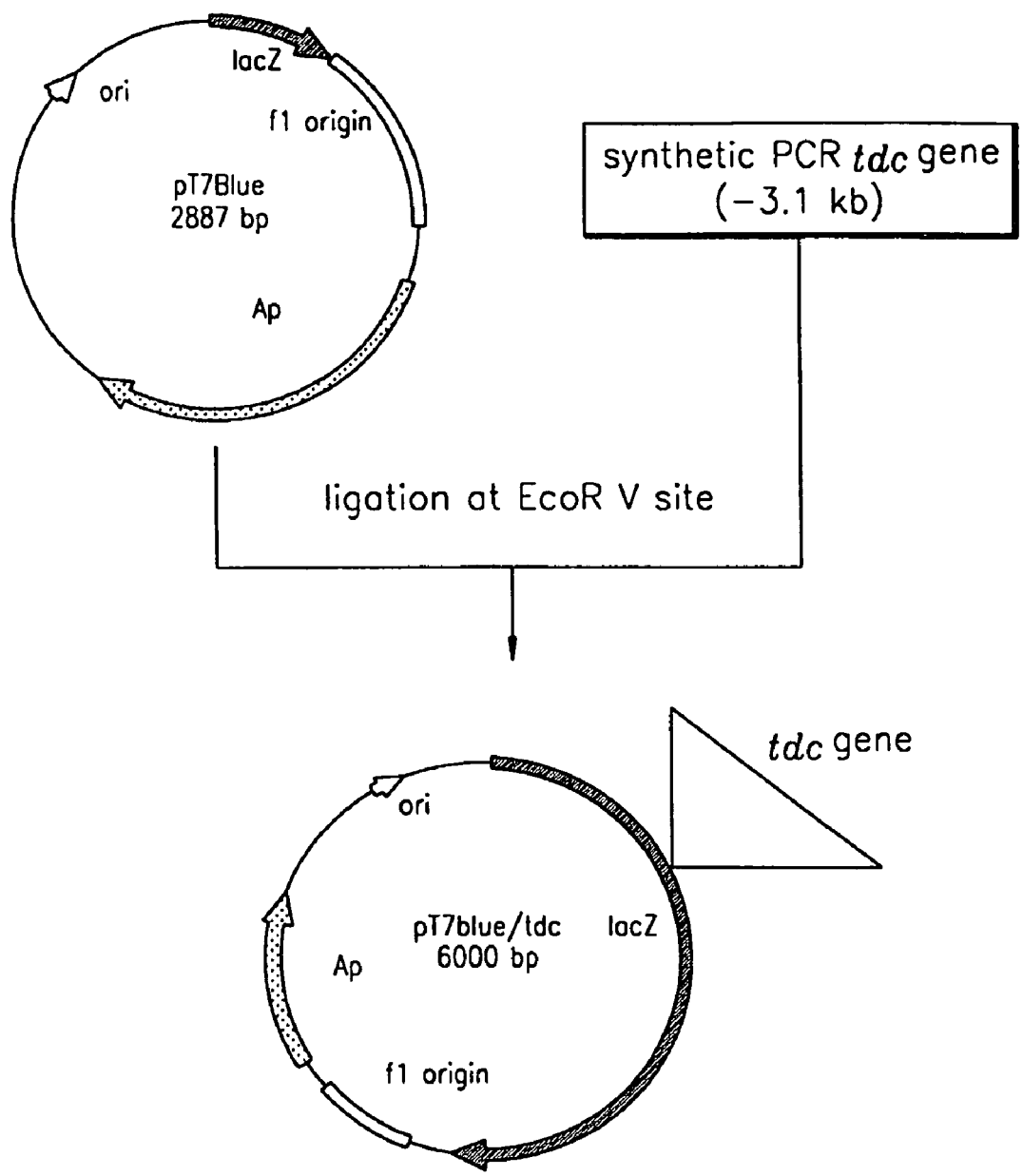
FIG. 1 depicts the process of constructing recombinant plasmid pT7Blue/tdc.

The PCR products were subjected to electrophoresis in 0.7% agarose gels to elute bands of a desired size. The eluted bands were ligated by blunt-end ligation with pT7Blue cloning vector (Novagen Co.) overnight at 16° C. to obtain recombinant plasmid pT7Blue/tdc (see FIG. 1). E. coli DH5α was transformed with the resulting recombinant plasmid pT7Blue/tdc, plated on a solid medium containing 50 mg/L of ampicillin, and incubated overnight at 37° C.

Colonies were tooth-picked from the culture, inoculated into a 3-mL liquid medium, and incubated overnight at 200 rpm. Plasmid DNA was isolated from the culture using a QIAGEN mini prep. kit, and the size of the plasmid DNA was identified. The plasmid DNA was digested with restriction enzymes, Sma I and Pst I, and subjected to electrophoresis in 0.7% agarose gels to identify whether its orientation is tdc R-A-B-C. The identified plasmid DNA, pT7Blue/tdc, was digested with restriction enzymes, BgI II and Hpa I (of about 1.1 kb each), and the digest was loaded onto 0.7% agarose gels to elute bands of about 4.9 kb. The eluted bands were reacted with the Klenow enzyme to generate blunt ends. A kanamycin-resistant gene fragment of about 1.7 kb containing the lox p site that obtained by reacting plasmid pUG6 (Ulrich et al., A new efficient gene disruption cassette for repeated use in budding yeast, *Nucleic Acids Research*, 1996, 24, pp. 2519-2524) with restriction enzymes Hinc II and EcoR V, is ligated to the isolated fragment of pT7Blue/tdc by blunt end ligation, thereby resulting recombinant plasmid pT7Δtdc::loxpKan.

EXAMPLE 2

Screening of Strain Integrated with Recombinant Plasmid

E. coli DH5α was transformed with the recombinant plasmid pT7Δtdc::loxpKan, plated on a solid medium containing 50 mg/L of ampicillin and 15 mg/L of kanamycin, and incubated overnight at 37° C. Colonies were picked from the culture, inoculated into a 3-mL liquid medium containing ampicillin and kanamycin, and incubated overnight at 200 rpm. Plasmid DNA was isolated from the culture using a QIAGEN mini prep. kit, and the size of the plasma DNA was identified. The plasmid DNA was digested with a restriction enzyme and loaded onto 0.7% agarose gels to identify its orientation. The identified plasmid DNA was digested with restriction enzyme PVU II and subjected to electrophoresis in 0.7% agarose gels to elute a DNA fragment (Δtdc::loxpKan) of about 3840 bp. pGmTN-PPC12, a threonine producing strain, was transformed with the DNA fragment Δtdc::loxpKan by electroporation and plated on a kanamycin-containing solid medium to screen colonies, giving recombinant strains having the deactivated tdc gene.

EXAMPLE 3

Comparison of Theonine Productivity in Flask Cultivation for Obtained Recombinant Strains Thirty single colonies of the recombinant strains cultured in the solid medium containing kanamycin in Example 2 were screened for L-threonine productivity comparisons using threonine titer media in Erlenmeyer flasks. The composition of the threonine titer medium used in each case is shown in Table 1.

TABLE 1

Composition of Threonine Titer Medium

| Component | Amount per liter |
|---|---|
| Glucose | 70 g |
| $(NH_4)_2SO_4$ | 28 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| Calcium carbonate | 30 g |
| L-methionine | 0.15 g |
| Yeast extract | 2 g |
| pH 7.0 | |

Single colonies were cultured on LB solid media overnight at 32° C. in an incubator. 25 mL of the titer medium was inoculated with a loopful of each culture and incubated at 32° C., 250 rpm for 48 hours. The results of the analysis are shown in Table 2. 28 colonies of thirty colonies of the new recombinant strains show excellent productivity, including eight colonies that produced 26 g/L or greater threonine, compared to the host strain, pGmTN-PPC12, which produced 23 g/L of threonine. The recombinant strain, which recorded the highest threonine productivity at 27 g/L with a higher yield of about 17.4% than the host strain, was observed and named "TRN212". The mutant strain TRN212 was deposited Feb. 19, 2002 with the Korean Collection for Type Cultures (KCTC) and was given Accession Number KCCM-10353.

TABLE 2

Results of Flask Titer Test for Recombinant Strains

| L-threonine Concentration | 20-23 g/L | 23-24.5 g/L | 24.5-26 g/L | 26 g/L or greater |
|---|---|---|---|---|
| Colony Counts | 2 | 9 | 11 | 8 |

EXAMPLE 4

Confirmation of Knock-out of tdc Gene Using Southern Blotting Analysis

Southern blotting was performed to verify the specific knock-out of the tdc gene of the recombinant strain obtained in Example 3. The host strain pGmTN-PPC12 and the recombinant strain TRN212 (KCCM-10353) were incubated overnight in a 30 mL liquid medium at 200 rpm, and genomic DNA was isolated using a QIAGEN genomic kit 20. The isolated genomic DNA was digested with restriction enzyme EcoR I and subjected to electrophoresis in 0.7% agarose gels to separate DNA fragments by size. The size-separated DNA fragments were attached to a nylon membrane (YOUNG Sci. Biodyne B Membrane) overnight by capillary transfer (Molecular Cloning, Vol. 1, 6.31-6.38) of the electrophoretic gel, followed by dehydration and UV radiation (120 mJ/cm², SpectroLinker™) to immobilize the DNA fragments on the nylon membrane (Molecular Cloning, Vol. 1, 6.45). The DNA fragments affixed to the nylon membrane was prehybridized in Prehybridization Buffer I (Roche #1093657) at 55° C. for 2 hours and then hybridized in a hybridization oven (BAMBINO 230300) with addition of previously prepared denatured DNA probe.

The denatured probe used was prepared as follows. Plasmid pUG6 isolated using a QIAGEN kit was digested with restriction enzymes, Hinc II and EcoR V, to obtain a kanamycin-resistant gene fragment of about 1.7 kb that contained the lox p site. This gene fragment was heated in 100° C. boiling water for 5 minutes and cooled using ices for 5 minutes to generate single-stranded DNAs. The single-stranded DNAs were reacted overnight at 37° C. using a DIG Labelling and Detection Kit (Roche #1093657) to generate DIG-UDP-integrated DNA probes.

Figure 3:
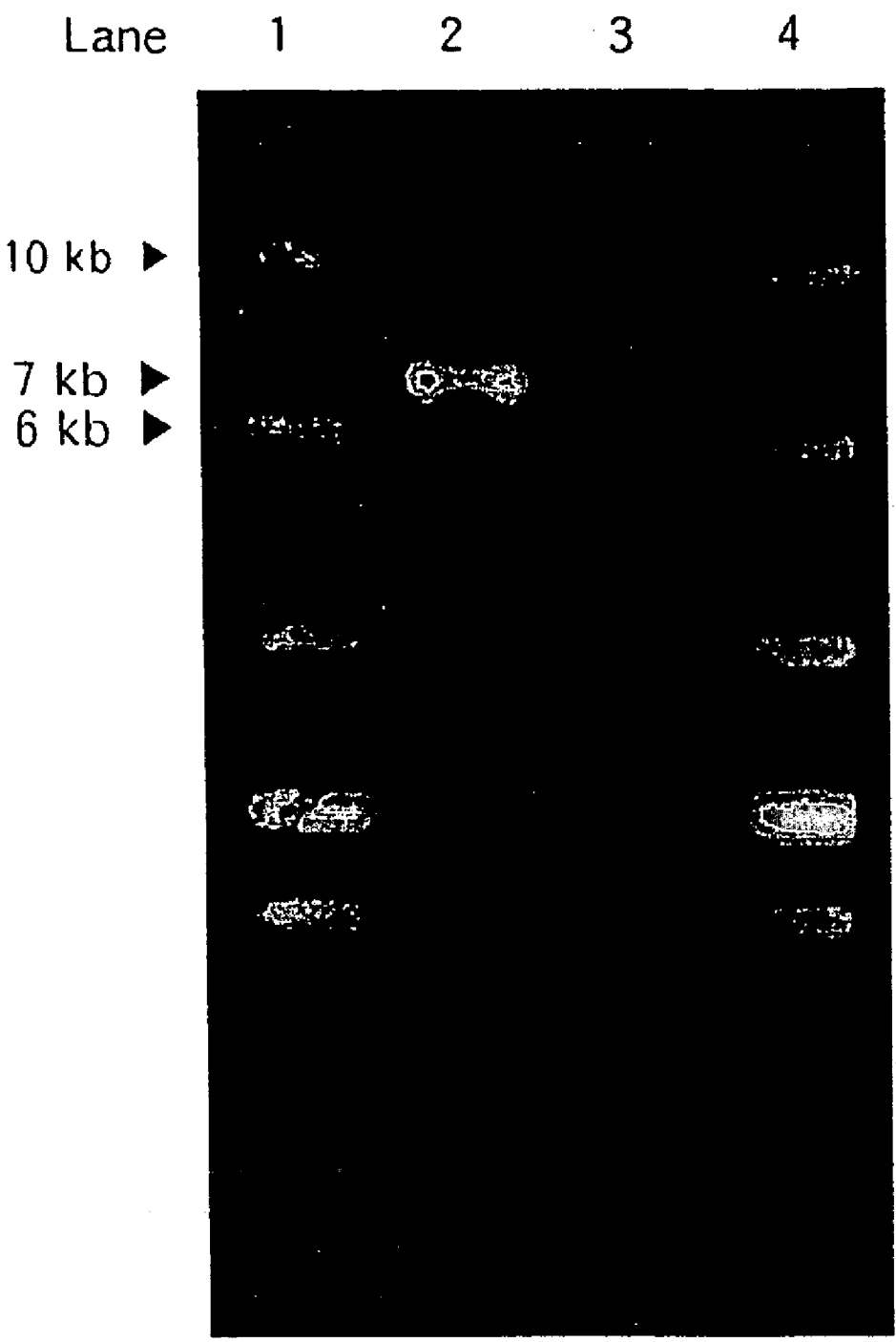
FIG. 3 shows the results of a Southern blot analysis obtained by image scanning using a FLA-5000 imaging system (FUJIFILM), where Lanes 1 and 4 indicate size markers, and Lane 2 and 4 indicate TRN212 (KCCM-10353) and host strain pGmTN-PPC12.

After hybridization, the DNA fragments non-specifically bound to the membrane were removed using Washing Solutions I and II (Roche #1093657). Then, the membrane was treated with Prehybridization Buffer 2 (Roche #1093657) at room temperature for 30 minutes for masking and reacted with an addition of anti-DIG antibody that is specifically coupled to DIG-UTP, at room temperature for 30 minutes. The anti-DIG antibody non-specifically bound to the membrane was removed using Washing Solution III (Roche #1093657), and the membrane was subjected to color reaction using a Labelling and Detection kit (Roche #1093657) until bands appeared. The results are shown in FIG. 3. No band appeared for the host strain pGmTN-PPC12 (Lane 1) without the kanamycin gene. In contrast, a band of about 7 kb was observed in Lane 2 for the new recombinant strain according to the present invention, TRN212 (KCCM-10353), which was expected. A tdc gene fragment of about 5.3 kb resulting from the digestion with restriction enzyme EcoR I and the kanamycine-resistant gene of about 1.7 kb amount to about 7.0 kb. Lane 1 and Lane 4 represent size markers.

EXAMPLE 5

Comparison of L-threonine Productivity Using Fermentor

L-threonine productivity in a 5-L fermentor was compared between host strain pGmTN-PPC12 and recombinant strain TRN212 (KCCM-10353) having the deactivated tdc gene, which had been screened in Example 2 and undergone the test to confirm the knock-out of the gene in Example 4. The initial medium composition used is shown in Table 3. LB media further containing per liter 10 g of glucose and 0.1 g of L-methionine were used for seed culture, and an initial volume of inoculation into a fermentor was determined at 3-5% by volume of a target initial culture. Glucose was added to a final concentration of 5% by weight each time, over 6 times in total, along with 1% by weight of $KH_2PO_4$. Here, each addition of glucose was determined by deletion of glucose. The initial volume of the culture was 1.5 L and the final volume of the culture was 3.0 L. A total concentration of glucose added through fermentation was 250 g/L. During fermentations, the medium was stirred at 700-1000 rpm, temperature was controlled at 32° C., and pH was adjusted at 7.0 with 25-28% ammonia water. Air-flow velocity was adjusted at 0.5 vvm. The results are shown in Table 4. As shown in Table 4, the host strain TRN212 produces 93.5 g/L of L-threonine with a yield of 37.4% with respect to glucose consumption. In contrast, recombinant strain TRN212 produces 112 g/L of L-threonine with a yield of 45.2%, which is 21% higher than the host strain TRN212. In addition, a similar fermentation pattern as the host strain was observed on the recombinant strain, without reduction in sugar consumption during fermentation, which often appears on recombinant strains due to growth inhibition.

TABLE 3

Initial Medium Composition in 5-L Fermentor

| Component | Amount per liter |
|---|---|
| Glucose | 50 g |
| $KH_2PO_4$ | 4 g |
| $(NH_4)_2SO_4$ | 6 g |
| Yeast extract | 3 g |
| $MgSO_4 \cdot 7H_2O$ | 2 g |
| L-methionine | 1 g |
| $FeSO_4 \cdot 7H_2O$ | 40 mg |
| $MnSO_4 \cdot 8H_2O$ | 10 mg |
| $CaCl_2 \cdot 2H_2O$ | 40 mg |
| $CoCl_2 \cdot 6H_2O$ | 4 mg |
| $H_3BO_3$ | 5 mg |
| $Na_2MoO_4 \cdot 2H_2O$ | 2 mg |
| $ZnSO_4 \cdot 7H_2O$ | 2 mg |
| pH 7.0 | |

TABLE 4

Results of Fermentative Production of Threonine by Recombinant Strains

| Strain | Threonine (g/L) | Fermentation Time (hr) | Yield (%) |
|---|---|---|---|
| PGmTN-PPC12 | 93.5 | 78 | 37.4 |
| TRN212 | 112 | 77 | 45.2 |

The new recombinant strain of the present invention is used in producing L-threonine, both amount and yield are improved greater than 20% compared to the host strain, without reduction in sugar consumption during fermentation, which often appears on recombinant strains due to growth inhibition.

What is claimed is:

1. Threonine-producing *E. coli* strain TRN212 deposited under Accession No. KCCM-10353.

2. A method for producing L-threonine comprising culturing the *E. coli* strain of claim 1 and thereby produce L-threonine.

* * * * *